United States Patent [19]

Flower

[11] Patent Number: 4,485,820

[45] Date of Patent: Dec. 4, 1984

[54] METHOD AND APPARATUS FOR THE CONTINUOUS MONITORING OF HEMOGLOBIN SATURATION IN THE BLOOD OF PREMATURE INFANTS

[75] Inventor: Robert W. Flower, Cockeysville, Md.

[73] Assignee: The Johns Hopkins University, Baltimore, Md.

[21] Appl. No.: 376,784

[22] Filed: May 10, 1982

[51] Int. Cl.³ .............................................. A61B 5/00
[52] U.S. Cl. .................................... 128/633; 128/634; 128/745; 351/219; 356/41
[58] Field of Search ........ 128/633, 634, 745, 664–666; 356/41; 351/219

[56] References Cited

U.S. PATENT DOCUMENTS

| 4,169,664 | 10/1979 | Bailey | 351/219 X |
| 4,295,470 | 10/1981 | Shaw et al. | 128/634 |
| 4,305,398 | 12/1981 | Sawa | 128/633 |
| 4,350,163 | 9/1982 | Ford et al. | 128/633 |

FOREIGN PATENT DOCUMENTS

| 0806003 | 2/1981 | U.S.S.R. | 128/745 |

OTHER PUBLICATIONS

Laing et al., IEEE Trans. of Biomed. Eng., vol. BME-22, No. 3, pp. 183–195, May 1975.
Laing et al., Arch. Ophthalmol. vol. 93, Feb. 1975, pp. 143–145.
Cohen et al., IEEE Trans. on Biomed. Eng. vol. BM-23, No. 5, Sep. 1976, pp. 391–400.

Primary Examiner—Kyle L. Howell
Assistant Examiner—John C. Hanley
Attorney, Agent, or Firm—Robert E. Archibald; Howard W. Califano

[57] ABSTRACT

A method and apparatus is disclosed for continuously monitoring hemoglobin saturation in the blood of premature infants. A substantial portion of the eye fundus is illuminated by passing at least two frequencies of light through the pupillary opening. The light scattered from the fundus is collected as it passes out through the pupillary opening and its intensity is measured. Calculations known in the art are used to determine blood hemoglobin based on the intensity of the scattered light. A contact lens with associated fiber optic links is used to illuminate the infant eye and to collect the scattered light.

6 Claims, 6 Drawing Figures

METHOD AND APPARATUS FOR THE CONTINUOUS MONITORING OF HEMOGLOBIN SATURATION IN THE BLOOD OF PREMATURE INFANTS

STATEMENT OF GOVERNMENTAL INTEREST

The invention herein described was made in the course of or under a grant or award from the Department of Health and Human Services.

TECHNOLOGICAL CONTEXT OF THE INVENTION

In caring for and administering to the needs of the premature infant, a vital parameter that is sought to be measured is the level of oxygen saturation in the arterial blood flowing from the heart of the infant to various other organs, such as the brain and the eye. The measurement of this parameter is critical in that too much or too little oxygen in the blood can produce damaging effects. If an infant has too little oxygen in his blood, he can develop respiratory distress. The infant can become cyanotic if oxygen insufficiency continues, and death ensues. On the other hand, if the blood is excessively saturated with oxygen for a long period of time, retinolental fibroplasia (RLF) leading to blindness can result.

Physicians interested in measuring or monitoring the amount of oxygen in the blood, i.e., hemoglobin (Hb) saturation, have employed various methods. According to one method, the physician obtains a small sample of blood by sticking the heel of the infant, and places the sample in a machine which analyzes it. Where continuous monitoring is desired in the case of a premature infant receiving oxygen thereapy, such "heel sticking" might be desired as frequently as at five minute intervals. Another invasive technique employs an umbilical artery catheter through which blood samples are taken. Catheter clotting, however, can restrict the taking of samples. When numerous samples are taken, such invasive techniques have the notable disadvantage of decreasing the amount of blood in the body, which could lead to anemia. Moreover, these two techniques to do not generated information necessarily indicative of the amount of oxygen in the blood flowing to the head and nourishing the brain; but instead it provides information as to oxygen saturation in the lower portions of the body.

Conditions may exist wherein the oxygen content of arterial blood flowing to various parts of the body may differ markedly. For example, during fetal development there exists communications between the left and right sides of the heat (the foramen ovale and the ductus arteriosis which facilitate the blood gas exchange mechanisms between mother and fetus). Normally, upon birth, these heart shunts close to order to isolate arterial from venous blood. If they do not close, however, blood from heel-sticks will not necessarily indicate that this condition exists and that the blood supply to the brain may be affected. To determine the oxygen saturation of blood to the brain and eyes it is thus advisable to monitor the arterial blood flowing to those organs more directly.

Various non-invasive techniques have been suggested by previous and contemporary authors and inventors which seek to overcome the disadvantages of the heel stick and umbilical artery blood analysis techniques. For example, Cohen and Laing in an article entitled "Multiple Scaterring Analysis of Retinal Blood Oximetry", *IEEE Transactions on Biomedical Engineering*, Vol. BME-23, No. 5, September 1976 and Laing et al in an article entitled "The Choroidal Eye Oximeter: An Instrument for Measuring Oxygen Saturation of Choroidal Blood In Vivo", *IEEE Transactions of Biomedical Engineering*, Vol. BME-22, No. 3, May 1975, disclose various types of oximeters used in measuring hemoglobin saturation in the blood vessels of the eye by use of a fundus camera. Such references teach the use of a fundus camera to *image* the ocular blood vessels by shining light into the eye and measuring the amount of light, at each of several frequencies, which is reflected from the fundus. In essence, these techniques shine a beam into the eye and measure the light exiting from the eye. The problems with the methods suggested by Cohen and Laing as well as Laing et al are several. First, these techniques require the use of a fundus camera which is generally large and requires a substantial power supply; continuous monitoring with such cumbersom apparatus, especially in a nursery, is impractical. Second, the accuracy of these techniques varies.

With regard to examining retinal blood flow, various factors exist which render these techniques somewhat inapposite for measuring oxygen saturation in the premature infant eye. Unlike the adult, the infant does not have a completely vascularized retina. In addition, comparing the retinal and the choroidal circulations, retinal arterial blood oxygen saturation is considerably different from that of retinal venus blood saturation whereas the choroidal arterial and venus oxygen saturations differ by only several millimeters of mercury. Because of the large volume of the choroidal vasculature and the large volume blood flow through it, all choroidal blood may be considered as maintaining the initial level of arterial oxygen saturation which is the information desired in infant monitoring. Laing et al makes note of this feature of the choroid stating that "no distinction is generally made between choroidal venus and choroidal arterial blood". Like Cohen and Laing, however, Laing et al uses an imaging technique which requiring an elaborate optical system including a fundus camera. In particular, Laing et al suggests the focusing of a light beam on the fundus, or more particularly the choroid, and measuring the intensity of light diffusely reflected from individual choroidal blood vessels at two wavelengths. Considerable discussion regarding the pigment epithelium layer of the adult eye which is between the sensory retina and the underlying choroidal vasculature is made, and it is suggested that the epithelial layer effects the intensity measurements obtained by the system in Laing et al. Laing et al illuminates and examines an area within the fundus extending approximately 28°. An average of the light intensity over that area is taken to provide a measure of oxygen saturation at that area in the eye. One of the major drawbacks with the Laing et al system was recognized by the authors who state that "head and eye movements during the measurement period are capable of introducing considerable noise". Because the Laing et al system employs a fundus camera which looks into the eye and employs a beam of light which is directionally sensitive, such body movements can cause serious, undesirable effects on measurement accuracy.

Others in the field of oximetry have noted that light striking a sample of blood is diffusely reflected and that the diffusion is related to the level of oxygen saturation. Paul in an article entitled "Oximetry", *IRE Transactions* on *Medical Electronics*, pages 34–38, July 1958; Millikin in an article entitled "The Oximeter, an Instrument for Measuring Continuously the Oxygen Saturation of Arterial Blood in Man", *The Review of Scientific Instruments*, Vol. 13, pages 434–444, 1942; Poulanjie in "New Reflection Oximeter", *The Review of Scientific Instruments*, Vol. 31, No. 4, April 1960; and Shaw in various patents (such as U.S. Pat. Nos. 4,114,604, 3,847,483, and 3,638,640) discuss the reflectance of light from the surface of the skin of the forehead and its transmittance through the ear to obtain arterial oxygen saturation measurements. These various references are all non-invasive, are intended for continuous use, and are not particularly cumbersome in size, thereby improving on the invasive techniques previously used.

The Shaw patents show various types of oximeters which are of the non-invasive variety. U.S. Pat. No. 3,638,640 teaches an oximeter method and apparatus whereby radiation is directed into skin tissue at a plurality of wavelengths and the intensity of radiation passing therethrough or being reflected thereby is measured to indicate the concentration of oxyhemoglobin in the total concentration of hemoglobin, i.e., the oxygen saturation, of a subject. In this reference, Shaw refers to the ear and the forehead in particular as portions of the body at which such measurements can be taken. U.S. Pat. No. 3,847,483, however, discloses an optical oximeter wherein fiberoptic guides are arranged within a double lumen catheter which is inserted in a blood vessel in order to detect oxygen saturation. In the Background of the Invention of U.S. Pat. No. 3,847,483, there is a discussion of various catheter techniques for measuring oxygen saturation, indicating the various problems encountered with such techniques. In the Background discussion, conventional theory regarding the determination of oxygen saturation is provided and a standard equation for determining oxygen saturation is repeated, namely:

$$\text{Oxygen Saturation} = A + B \frac{I_1}{I_2}$$

In this equation, $I_1$ is the light intensity diffusely back scattered from the Blood at the "isobestic" wavelength (i.e., the wavelength at which little or no difference appears in the optical reflectance of oxyhemoglobin versus reduced hemoglobin); $I_2$ is the light intensity diffusely back scattered at a nonisobestic wavelength; and A and B are experimentally determined calibration constants. Shaw et al discuss possible errors in the above simple equation of oxygen saturation and determine a more complex equation which does not require either wavelength to be isobestic. In particular, Shaw discloses an equation for oxygen saturation to be:

Oxygen Saturation $= A0 + A1 \times I_1 + A2 I_2 / B0 + B1 \times I_1 + B2 \times I_2$ where A0, A1, A2, B0, B1, B 2 are all calibration coefficients and $I_1$ and $I_2$ are backscattered light intensities of two differing wavelengths. Shaw in U.S. Pat. No. 4,114,604, improves on the equation further by defining oxygen saturation in numerous other equations where three optical wavelengths are employed to accurately determine oxygen saturation. In particular, three equations are advanced by Shaw which enhance the oxygen saturation determination (OS):

$$os = \frac{A_0 + A_1 \left(\frac{I_1}{I_2}\right) + A_2 \left(\frac{I_3}{I_2}\right)}{B_0 + B_1 \left(\frac{I_1}{I_2}\right) + B_2 \left(\frac{I_3}{I_2}\right)}$$

$$os = \frac{A_0 + A_1 \left(\frac{I_1}{I_2}\right) + A_2 \left(\frac{I_1}{I_2}\right)^2 + A_s \left(\frac{I_3}{I_2}\right)}{B_0 + B_1 \left(\frac{I_1}{I_2}\right) + B_2 \left(\frac{I_1}{I_2}\right)^2 + B_3 \left(\frac{I_3}{I_2}\right)}$$

$$os = \frac{\Sigma A_i R_i^j}{\Sigma B_i R_i^j}$$

where subscripted A's are weighting coefficients and $R_i$ is the ratio of normalized light intensities measured at the three wavelengths.

Apparatus for processing the signals generated at the three wavelengths is described in detail in U.S. Pat. No. 4,114,604.

SUMMARY OF THE INVENTION

The present invention overcomes numerous disadvantages of prior and current technologies by considering the fundus of the eye, more specifically the choroid, to be an integrating sphere rather than merely a surface upon which light is specularly reflected.

The present invention employs light intensity measurements at a plurality of wavelengths to determine the oxygen saturation of blood in the choroid of the eye. Unlike other techniques for measuring oxygen saturation by introducing light into the eye, the present method and apparatus seeks to illuminate as much of the inner surface of fundus of the eye as possible and detect light emanating from as large a fundus area as possible in order to make intensity measurements. Where other inventions have considered the directionality of light entering and exiting from the eye as crucial in their measurements and seek to eliminate the effects of diffused light reflecting off portions of the fundus which are not directly illuminated by the incoming light, the present invention makes use of these light intensity data previously considered undesirable.

Known technology is best characterized as area specific. That is, light entering the eye is directed to a particular area of the fundus under examination. The present invention is, contrarily, not area specific and does not rely upon directly reflected light but, instead, involves detecting light which is reflected (or multiply reflected) from fundus areas.

In order to utilize the non-area specific aspect of the present invention, a photodetector is placed in close proximity to the cornea of the eye, centered with respect to the papillary opening. This permits collection of any reflected light which exits from the eye, whether directly or multiply reflected from the fundus. Such detection is best characterized as omnidirectional. As the distance of the detector from the cornea increases, the system becomes increasingly area specific. Placement of the detector in close proximity to the cornea is, therefore, extremely important. It is thus an object of the invention to provide omnidirectional detection which alleviates the need for elaborate optical equipment which focuses and directs a beam of light to a specific portion of the inner eye or which must form and relay an image of the fundus.

As the omnidirectional detection of light over the entire fundus is an object of the present invention, it is also an object to introduce into the eye light which impinges upon the greatest possible fundus surface area. The source of light is thus also omnidirectional, being placed near the cornea and centered with respect to the papillary opening. In order to achieve relatively even illumination within the eye, it is an object of a preferred embodiment of the invention to provide a plurality of optical transmitters annularly disposed about a point photodetector. Each transmitter provides light at one of a plurality of wavelengths and the transmitters are positioned at distances far enough from each other to prevent significant signal interference and cross-talk.

To further achieve uniform illumination, it is still another object of the above preferred embodiment to provide a geometrically symmetrical arrangement of the transmitters relative to each other and the papillary opening of the eye.

It is yet a further object of the present invention to provide, as an alternative source of light, a fiberoptic element positioned near the cornea of the eye for providing light at a plurality of specific wavelengths. According to this embodiment, the light source can be at the center with the detector being an annular element surrounding the source. While this alternative embodiment may not provide the noise or interference immunity of the previously discussed embodiment having the detector encircled by the transmitters, the alternative embodiment does feature symmetry and obviates the need for a plurality of light sources, where the fiberoptics can provide a plurality of signals from the same source.

It is still yet another object of the present invention to determine light intensity measurements of the choroid of a premature infant where the inside of the eye is treated as an integrating sphere and such measurements are processed to provide essentially continuous blood oxygen saturation data. The infant eye has a retina which is not fully vascularized and does not yet have significant pigmentation as in the adult eye. It is thus possible to treat light reflected from a large ocular fundus area as if the light were reflected primarily by arterialized blood by recognizing that the choroidal blood is the dominant contributor to the integrating sphere phenomenon which is observed to occur in the immature eye. It is upon this realization that the present invention for monitoring the arterial blood oxygen saturation of the infant is based.

DETAILED DESCRIPTION OF THE PREFERRED EMBODIMENT

Figures 1A, 1B, 2, 3:
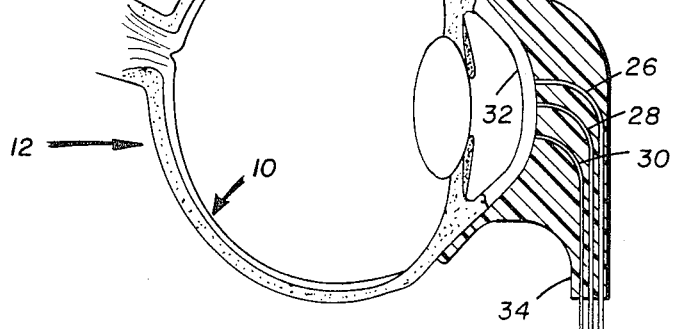
FIG. 1A is an enlarged cross-sectional view of the human eye.
FIG. 1B is an enlarged cross-sectional view of the fundus wall.
FIG. 2 is a cross-sectional view of the human eye showing the placement and design of the invented contact lens oximeter.
FIG. 3 is a frontal view of the human eye showing the placement and design of the invented contact lens oximeter.

FIG. 1A shows an enlarged representation of the human eye. The fundus 10 of the eye 12, which is generally the area of the inner eye oppositely disposed from the pupil 14, contains the sensory retinal layer 16, the pigment epithelium 18, a choroidal layer 20, and the sclera 22. In the mature adult eye the pigment epithelium 18 (as can best be seen in FIG. 1B) is dense and blocks light penetration into the choroidal layer 20. However, in the premature infant eye, the pigment epithelium 18 has not fully developed and is not optically dense. Therefore, light impinging upon the fundus of the premature infant's eye penetrates the pigment epithelium 18 and is reflected from blood vessels within the choroidal layers 20. Since capillaries of the retinal vasculature are small and infrequent compared to those of the choroidal vasculature, the majority of the light will be reflected from blood within choroidal blood vessels, especially the chorcapillaries which occupy the plane just beneath the pigment epithelial layer. Therefore, the majority of light entering the premature infant eye will be reflected from capillaries of the choroid. The small amount of light reflected from the retinal vasculature may be treated as an insignificant level of noise.

The circulation of blood in the choroid is also unique in that it is so great and rapid that there is little difference between the hemoglobin saturation in the choroidal capillaries and that in the choroidal arteries. Therefore, by observing oxygen saturation in the choroidal capillaries, one can obtain an accurate representation of oxygen saturation in arterial blood being carried to the brain.

The present inventor combined these presently unexploited scientific notions which known oximetric techniques and has developed a method and apparatus for continuous non-invasive in situ hemoglobin saturation level monitoring in premature infants. The invented method generally involves illuminating the eye with diffused light at various frequencies and measuring the intensity of light reflected back from the choroidal blood circulation. In specific, a light source capable of generating several frequencies of light and having a broad beamwidth, or being omnidirectional, is brought in close proximity to the cornea of the eye in order to illuminate a substantial portion of the fundus area with diffused illumination. Secondly, the scattered light produced by repeated reflections of the illuminating light from the choroidal capillary layer is detected by a photodetector placed in close proximity to the cornea. As scattered light passes out through the pupillary opening, it is detected by the photodetector, and the intensity of the scattered light is measured at the various frequencies corresponding to those introduced into the eye. This information can then be used to calculate the hemoglobin saturation level by performing calculations well known in the art. These calculations are described in the following publications which are incorporated herein by reference: "Oximetry", *IRE Transactions on Medical Electronics,* pages 34–38, July 1959; "The Oximeter, and Instrument for Measuring Continuously the Oxygen Saturation of Arterial Blood in Man", *The Review of Scientific Instruments,* Vol. 13, pages 434–444, 1942; "New Reflection Oximeter", *The Review of Scientific Instruments*, Vol. 4, page 31, April 1960; and the following Patents issued to Shaw, U.S. Pat. Nos. 4,114,604, 3,847,483, and 3,638,640.

FIG. 2 outlines the preferred apparatus for illuminating the infant eye and detecting light scattered by the fundus. An especially adapted contact lens 24, usually a scleral contact lens, contains a plurality of fiberoptic elements 26, 28 and 30 incorporated into the lens. The fiberoptic elements can be affixed to the lens with epoxy or other conventional means. The fiberoptic elements can either transmit light into the eye from a light source (not shown) or receive light scattered by the eye fundus 10. The lens 24 is shown fitting over the cornea 32 of the eye 12. Extending from, and integral with, the contact lens 24 is a flexible portion 34 which encloses the fiberoptic elements 26, 28, and 30. This flexible portion 34 and the contact lens 24 may be opaque except for small areas which allow the fiberoptic elements to transmit light into or receive light from the eye.

FIG. 3 provides a frontal view of the eye and the contact lens 24. In addition to elements 26, 28 and 30, other fiberoptic elements 36 through 48 are also shown. The number of fiberoptic elements may vary and may in fact increase to form a nearly continuous annulus 50 (shown in dotted lines) about the center element 28. The center element 28 may comprise a single fiberoptic element or a cluster of fiberoptic elements. In accordance with the invention shown in FIGS. 2 and 3, the fiberoptic center elements 28 can be employed as a transmitter and the remaining elements can serve as receivers. Conversely, center elements 28 can represent a receiver with the annular element (elements 26, 30 and 38 through 48) serving as transmitter elements. In either case, optical signals at various selective wavelengths are transmitted into the eye through the fiberoptic elements and scattered radiation is subsequently received for processing by additional fiberoptic elements.

According to the invention, the transmitted signal does not focus on any particular artery or blood vessel as in the case with other prior art oximeters. More specifically, the optical signal is not directed or focused onto the retinal arteries or veins or through voids in the pigment epithelium layer onto arterial or venous blood vessels in the choroid. The present invention transmits a diffused or broad beam of light which is reflected principally from capillary vessels in the choroid the choriocapilloria). Similarly, the fiberoptic receiving elements do not focus on a particular spot in the eye. Rather, the fiberoptic receiving elements receive scattered light which passes out through the pupillary opening. The fiberoptic receiving element generally acts as an omnidirectional or broad beam detector.

Figure 4:
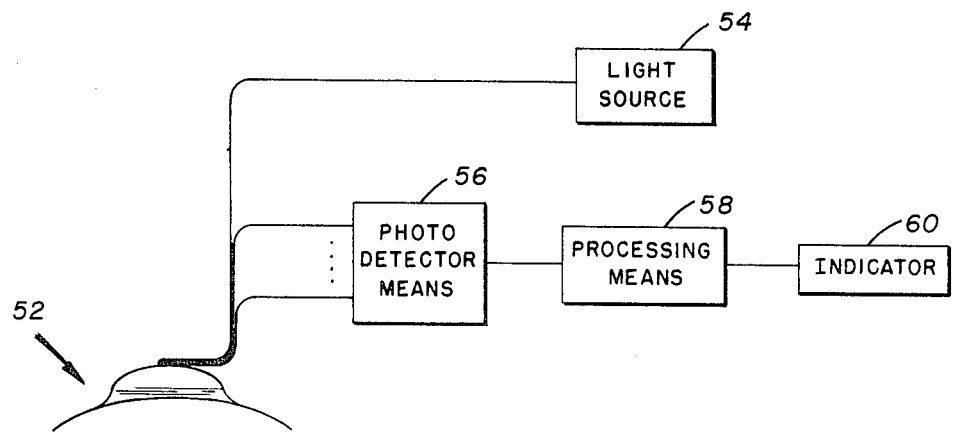
FIG. 4 is a block diagramatic drawing showing the interface of the contact lens oximeter with detection and processing circuitry.

FIG. 4 illustrates, in block diagramatic form, the interface of the contact lens oximeter 52 illustrated in FIGS. 2 and 3 with the prior art oximeter detection circuitry. The transmitter fiberoptic elements are connected to a light source 54 which generates the selected light frequencies necessary for optical oximetry. The literature indicates that measurements should be made for at least two selected frequencies. One selected frequency may be at the isobestic frequency of 850 nanometers, a frequency where hemoglobin saturation does not affect the amplitude of the scattered light. Other frequencies could be selected from wavelengths between 420 nanometers and 900 nanometers, with 640 nanometers and 680 nanometers being preferred wavelengths. By comparing the amplitude of the scattered radiation for various non-isobestic wavelength with the amplitude of the scattered light at an isobestic wavelength (850 nanometers) a measurement of hemoglobin saturation can be calculated.

The receiver fiberoptic elements which collect the scattered light are connected to a photodetector means 56. The photodetector means 56 measures the intensity of the light received for each of the selected transmitted light frequencies. The signal from the photodetector means 56 is sent to a processing means 58, which amplifies the signal and calculates hemoglobin saturation based on known algorithms. An indicator means 60 is connected to the processor means 58 and displays in readable form the hemoglobin saturation level.

Several schemes are possible for switching between the several selected frequencies needed for optical oximetry. In one embodiment the light source may be time-modulated, switching between the desired illumination light frequencies. The fiberoptic link will carry the time-modulated light signals to the optical elements which transmit light into the infant's eye. The fiberoptic receiver elements collect the light scattered in the eye and are connected to several photodiodes within the photodetector means 56. The fiberoptic link contains appropriate optical filters such that each or several elements may detect the signal at only one of the selected wavelengths. For example, a 850 nanometer wavelength signal may be detected by elements 26 and 30 whereas a 640 nanometer wavelength signal may be detected by elements 38 and 40. In an alternative embodiment, each time-modulated frequency can be sent through separate fiberoptic links to selected transmitter fiberoptic elements in the annulus. In this embodiment the scattered light is received by the center element 28 and processed accordingly. These embodiments are not position sensitive, and movement of the lens in the eye or movement of the eye will not adversely affect the measurements made by the invention.

Figure 5:
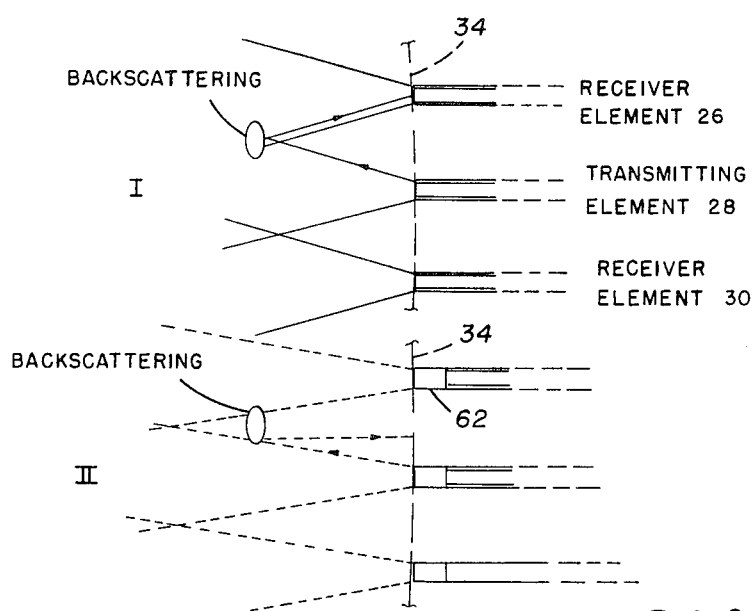
FIG. 5 is an enlarged view showing the placement of shading elements to eliminate backscattering and crosstalk.

The present invention also addresses the potential problem of backscattering and cross-talk between fiberoptic receiving and transmitting elements. Backscattering occurs when optical signals from the transmitter are reflected back by the cornea, and cross-talk occurs when light from the transmitted elements enters directly into the receiving elements. Backscattering and cross-talk signals may be erroneously detected by the receiving elements as light scattered from the blood. As shown in FIG. 5, the backscattering effects can be avoided by including cylindrical shading elements 62 at the respective points of transmission and reception by the fiberoptic elements. The solid lines shown in FIG. 5 correspond to the normal beam diversion of the transmitted and received signals. The dash lines represent the new diversions resulting from the emplacement of shading elements 62.

It will be noted that several other approaches are possible for introducing diffused light into the infant eye. A fundus camera can be used to illuminate the eye by first passing the beam through a diffuser such as a lens arrangement or curved reflecting mirror. In an alternative embodiment miniaturized transmitter and detector photodiodes may be mounted directly on the contact lens. However, all the various embodiments employ the same concepts, that diffused light is used to illuminate a substantial portion of the eye fundus, and light scattered by the eye fundus is received as it passes through the pupillary opening.

This method of monitoring hemoglobin saturation levels in infants can be best summarized as follows: First, several selected frequencies of light are used to illuminate a substantial portion of the eye fundus. Generally an isobestic wavelength and several non-isobestic wavelengths, usually, between 420 and 900 nanometers are selectively introduced into the infant eye. The illuminating light should be diffused or unfocused so that it illuminates as much of the fundus as possible. Second, light scattered by the fundus is received and its intensity is measured. The receiving means does not focus on a particular blood carrying vessel but detects light scattered by the inner surface of the eye which acts as an integrating sphere. The scattered light is principally reflected from choroidal capillaries and the intensity of the scattered light indicates properties of the capillary blood. Third, the intensity of the scattered light for each of the selected illuminating frequency is used to calculate the blood hemoglobin levels. This method may be used to measure the absolute hemoglobin level or to monitor relative changes in the hemoglobin level over an extended period of time.

Obviously many modifications and variations of the present invention are possible in light of the above teachings. It is therefore to be understood that within the scope of the appended claims the invention may be practiced otherwise than as specifically described.

What is claimed and desired to be secured by Letters Patent of the United States is:

1. An oximeter for continuous non-invasive monitoring of hemoglobin saturation levels in premature infants, comprising:

an opaque contact means, having a concave surface adapted to fit over the globe of a patent's eye, for mounting on the eye in communication with the outer surface of the eye cornea said contact means further having a plurality of holes therethrough with openings on the concave surface;

a light source capable of providing light at various frequencies;

at least one transmitting fiberoptic element means mounted into one of said holes, linking said contact means to said light source, for illuminating a substantial portion of the eye fundus;

at least one receiving fiberoptic element means mounted into one of said holes and terminating a predetermined distance from the concave surface of said contact means for collecting light scattered by a substantial portion of said eye fundus and for reducing the collection of cross-talk light from said at least one transmitting fiberoptic element means and light from said at least one transmitting fiberoptic element means which is backscattered by the cornea; and, a detector, processor and indicator circuit means, linked by said receiving fiberoptic element to said contact means, for measuring the intensity of light radiation scattered by said eye fundus and for calculating and indicating hemoglobin saturation based upon the intensity of said scattered light for various frequencies of said illuminating light.

2. The apparatus of claim 13 wherein said contact means is adapted to fit over at least a portion of the eye sclera.

3. The apparatus of claim 1 wherein a plurality of said at least one illuminating fiberoptic element means are mounted in an annular array of holes in said contact means; and, wherein said annular array encircles said receiving fiberoptic element means.

4. The apparatus of claim 1 wherein a plurality of said at least one receiving fiberoptic element means are mounted in an annular array of holes in said contact means; and, wherein said annular array encircles said illuminating fiberoptic element means.

5. The apparatus of claim 3 or 4 wherein said annular array is a continuous annulus.

6. An oximeter for continuous non-invasive monitoring of hemoglobin saturation levels in premature infants, comprising:

an opaque contact means, having a concave surface adapted to fit over the globe of a patient's eye, for mounting on the eye in communication with the outer surface of the eye cornea said contact means further having a plurality of holes therethrough with openings on the concave surface;

a light source capable of providing light at various frequencies;

at least one transmitting fiberoptic element means mounted into one of said holes and, terminating a predetermined distance from the concave surface of said contact means, linking said contact means to said light source, for illuminating a substantial portion of the eye fundus;

at least one receiving fiberoptic element means mounted into one of said holes and, terminating a predetermined distance from the concave surface of said contact means for collecting light scattered by a substantial portion of said eye fundus and for reducing the collection of cross-talk light from said at least one transmitting fiberoptic element means and light from said at least one transmitting fiberoptic element means which is backscattered by the cornea; and, a detector, processor and indicator circuit means, linked by said at least one receiving fiberoptic element means to said contact means, for measuring the intensity of light radiation scattered by said eye fundus and for calculating and indicating hemoglobin saturation based upon the intensity of said scattered light for various frequencies of said illuminating light.

* * * * *

UNITED STATES PATENT AND TRADEMARK OFFICE
CERTIFICATE OF CORRECTION

PATENT NO. : 4,485,820
DATED : December 4, 1984
INVENTOR(S) : Robert W. Flower

It is certified that error appears in the above—identified patent and that said Letters Patent is hereby corrected as shown below:

Column 10, line 6 (Claim 2) delete "13" and substitute --1--.

Signed and Sealed this

Ninth Day of July 1985

[SEAL]

Attest:

DONALD J. QUIGG

Attesting Officer     Acting Commissioner of Patents and Trademarks